United States Patent [19]

Watson

[11] Patent Number: 4,597,385

[45] Date of Patent: Jul. 1, 1986

[54] BIOPSY INSTRUMENT

[76] Inventor: Trevor F. Watson, 2319 Bluff Blvd., Columbia, Mo. 65201

[21] Appl. No.: 689,711

[22] Filed: Jan. 8, 1985

Related U.S. Application Data

[63] Continuation of Ser. No. 490,122, Apr. 29, 1983, abandoned.

[51] Int. Cl.⁴ ............................................. A61B 10/00
[52] U.S. Cl. .................................... 128/751; 128/318
[58] Field of Search ............... 128/749, 751, 305, 309, 128/314, 318; 30/349, 337, 278

[56] References Cited

U.S. PATENT DOCUMENTS

| | | | |
|---|---|---|---|
| 1,663,761 | 3/1928 | Johnson . | |
| 2,725,629 | 12/1955 | Todhunter | 30/260 |
| 2,994,321 | 8/1961 | Tischler | 128/2 |
| 3,353,531 | 11/1967 | Armao | 128/2 |
| 3,391,690 | 7/1968 | Armao | 128/2 |
| 3,404,677 | 10/1968 | Springer | 128/2 |
| 3,585,985 | 6/1971 | Gould | 128/2 |
| 3,608,544 | 1/1970 | Schnepper | 128/2 R |
| 3,651,811 | 3/1972 | Hildebrandt et al. | 128/303 |
| 3,840,003 | 10/1974 | Komiya | 128/2 B |
| 3,895,636 | 7/1975 | Schmidt | 128/305 |
| 3,964,468 | 6/1976 | Schulz | 128/2 B |
| 3,989,033 | 11/1976 | Halpern et al. | 128/2 B |
| 4,243,047 | 1/1981 | Olsen | 128/751 |

FOREIGN PATENT DOCUMENTS 695659  9/1979  U.S.S.R. ............... 128/751

Primary Examiner—Edward M. Coven
Attorney, Agent, or Firm—Kokjer, Kircher, Bradley, Wharton, Bowman & Johnson

[57] ABSTRACT

An instrument for removing a biopsy specimen from the cervix. The instrument is a forceps-like device having opposing jaws that open and close. A blade on one jaw has a cutting edge which includes a sharp point that initially undercuts the specimen. As the point emerges, the sides of the cutting edge slice the specimen away from the cervix. The other jaw has a pair of teeth which grip and stabilize the cervix and a recess which receives the blade when the jaws are closed. The blade is disposable and is attached to a block which has a dovetail joint with the jaw so that it can be slipped onto and off of the jaw for replacement of the blade.

17 Claims, 5 Drawing Figures

U.S. Patent  Jul. 1, 1986  4,597,385
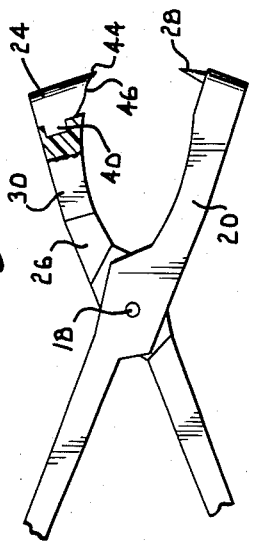
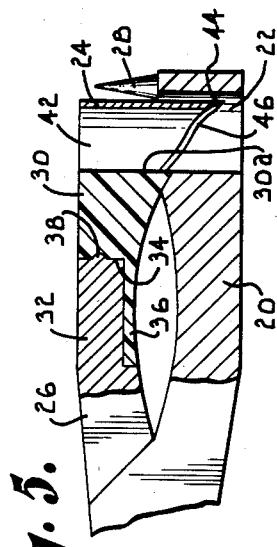
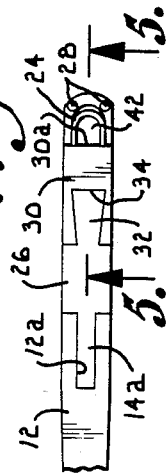
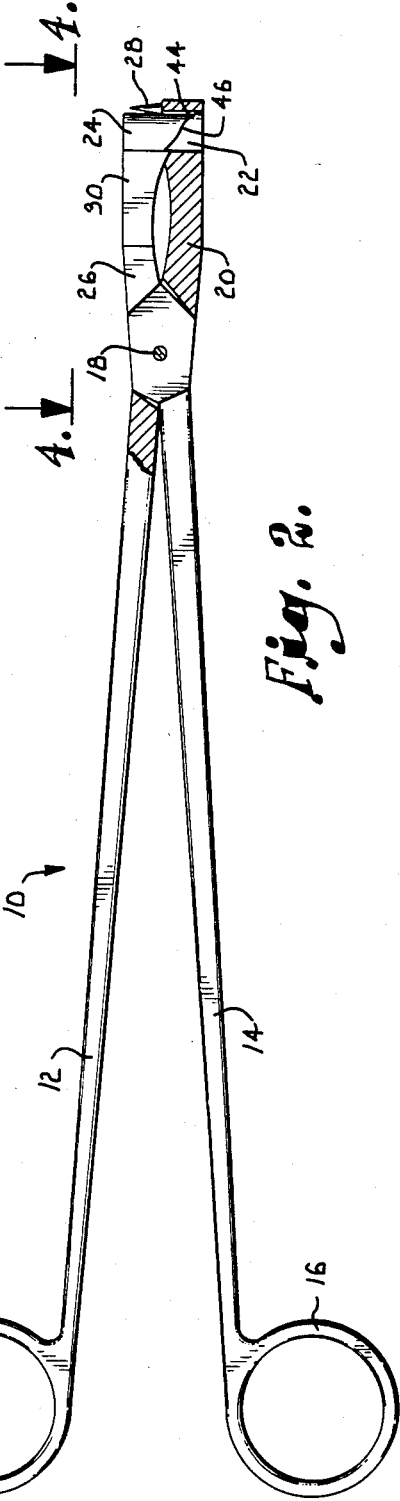

4,597,385

BIOPSY INSTRUMENT

BACKGROUND AND SUMMARY OF THE INVENTION

This invention relates in general to medical devices and more particularly to an instrument which is used to remove a cervical biopsy specimen.

In order to obtain good results from a cervical biopsy, it is necessary for the cervical specimen to consist of a full layer of cervical epithelium. In the past, various types of devices have been used to remove the biopsy specimen. The most popular devices in present use are the Kevorkian-Young forceps, the Gaylor forceps, the Schuber forceps, the VanDoren forceps and the Tischler forceps. Each of these instruments relies upon a pinching effect to obtain the biopsy specimen, and the pinching action causes the specimen to be crushed and otherwise unduly distorted. Also, the superficial epithelium is often scraped away such that a complete layer of cervical epithelium is not present in the specimen.

Other approaches that have been used to obtain cervical biopsy specimens have been even less satisfactory. The use of a punch followed by picking up of the specimen and undercutting it with a long handle scalpel has been proposed. However, this procedure inevitably results in excessive cutting of the specimen by the scalpel and in other mutilation which leaves the specimen in a poor condition for analysis.

It is therefore evident that a need exists for an instrument that is able to remove a complete and undeformed biopsy specimen from the cervix. The principal goal of the present invention is to meet that need.

More specifically, it is an object of the invention to provide a cervical biopsy instrument that avoids the use of pinching or crushing action in the removal of a biopsy specimen. In accordance with the invention, a unique blade is employed to initially undercut the specimen and then slice it away from the cervix as the blade moves from the undercut area toward the surface. This is accomplished by providing a blade that has a sharp point which penetrates the tissue and sides of the blade which slice the specimen away from the cervix as the jaws of the device are closed. As a result, there is no pinching action to crush or otherwise deform the specimen, and the surface epithelium is maintained intact with the remainder of the specimen.

Another object of the invention is to provide a biopsy instrument in which the blade can be quickly and easily removed after use and replaced with another clean sharp blade. The blade is attached to a block which has a dovetail connection with one jaw of the instrument. There is a stop at the dovetail joint which properly locates the block and a detent which holds it in place. After use, the block can be slipped off the jaw, and a replacement block can be installed in its place to provide a new blade.

A further object of the invention is to provide a biopsy instrument which firmly holds and stabilizes the cervix in the area where the biopsy specimen is to be removed. The teeth which are located next to the receiver securely grip the cervix to provide the required stability while the instrument is being operated to remove the biopsy specimen.

An additional object of the invention is to provide a biopsy instrument of the character described which is constructed in a simple and economical manner and which is safe and reliable in use.

Other and further objects of the invention, together with the features of novelty appurtenant thereto, will appear in the course of the following description.

DETAILED DESCRIPTION OF THE INVENTION

In the accompanying drawing which forms a part of the specification and is to be read in conjunction therewith and in which like reference numerals are used to indicate like parts in the various views:

FIG. 1 is a perspective view of a biopsy instrument constructed according to a preferred embodiment of the present invention, with the jaws in the fully open position;

FIG. 2 is a side elevational view of the biopsy instrument with the jaws in the fully closed position, with portions broken away for purposes of illustration;

FIG. 3 is a fragmentary elevational view of the jaws in the open position, with a portion broken away for purposes of illustration;

FIG. 4 is a fragmentary view taken generally along line 4—4 of FIG. 2 in the direction of the arrows; and FIG. 5 is a fragmentary sectional view on an enlarged scale taken generally along line 5—5 of FIG. 4 in the direction of the arrows.

Referring now to the drawing in more detail, numeral 10 generally designates a cervical biopsy instrument which is used to remove biopsy specimens from the cervix. The instrument 10 is a forceps type device having a pair of pincer arms 12 and 14. Each arm 12 and 14 has a handle end on which a loop 16 is formed to receive the fingers. Near the opposite or jaw end of arm 12, an opening 12a is formed to receive a necked down portion 14a of the other pincer arm 14. A pin 18 is extended through the portions of the two pincer arms which cross in order to pivotally connect the arms for opening and closing of the jaws as the looped handles 16 are moved away from and toward one another during use of the instrument.

The lower jaw 20 of the instrument is located on the end of arm 12. Jaw 20 is provided with a passage 22 which forms a recess for receiving a blade 24 carried on the upper jaw 26. The upper jaw 26 is located on the end of arm 14. A pair of sharply pointed teeth 28 are located on the lower jaw 20 near its free end and point toward the opposing jaw 26. The teeth 28 are used to penetrate the cervix in order to hold and stabilize it during use of the instrument, as will be explained more fully.

The blade 24 is a disposable blade which is attached to a block 30. The block 30 is in turn connected with the upper jaw 26 by a dovetail joint. The dovetail joint includes a tongue 32 which projects from the end of jaw 26 and has the shape of a dovetail. The adjacent end of block 30 has a dovetail groove 34 which extends from the upper surface of block 30 toward the opposing lower jaw 20.

As shown in FIG. 5, the dovetail groove 34 does not extend completely through block 30 but instead terminates at a finger 36 which is integral with block 30 and extends across the bottom of groove 34. The finger 36 serves as a stop which prevents tongue 32 from moving completely through groove 34 in a direction toward the lower jaw 20. When tongue 32 is in contact with the finger 36, the block 30 and blade 34 are properly positioned on jaw 26. A detent for releasably holding the block in place is formed by a small button 38 which projects from the free end of tongue 32. When the tongue is engaged against the finger 36, the button 38 snaps into a mating recess formed in block 30 at the base of groove 34, thereby holding the block 30 in place on the jaw 26.

The blade 24 is preferably constructed of a suitable metal and can be permanently attached to block 30 in any suitable manner. As shown in FIG. 3, the blade 24 may have a pair of projecting tabs 40 which are embedded in the free end of block 30. The block is preferably formed from a suitable plastic material. Block 30 has a flat outer surface 30a which is adjacent blade 24 and is both wider and longer than the blade. Surface 30a limits the depth of the bite that is taken by blade 24, as will be explained more fully.

The body of blade 24 is generally U-shaped in section and has a hollow interior which forms a cavity 42 in which the biopsy specimen is received as it is cut away from the cervix. The body of the blade 24 terminates in a bottom edge which acts as the cutting edge of the blade. The cutting edge is curved and includes a sharp point 44 located at the extreme outer end of the blade. On opposite sides of the point 44, the cutting edge includes side portions 46 which curve from the point 44 to the connection of blade 24 with the block 30. The passage serves as a receiver for the blade, as previously indicated, and the size and shape of passage 22 are suitable to receive the blade.

In use, the biopsy instrument 10 is applied to the cervix with the jaws 20 and 26 initially in the open position. The teeth 28 are set into the cervix in the area adjacent the cervical specimen which is to be removed for biopsy. The looped handles 16 are then moved toward one another to close the jaws and remove the biopsy specimen.

As the jaws close, the sharp point 44 initially penetrates the tissue and moves in an arcuate path as it approaches the receiver of the opposing jaw 20. As the point 44 undercuts the specimen, the sides 46 of blade 24 slice the specimen away from the cervix much in the manner of a scalpel. When the jaws have been fully closed in the position of FIG. 2, the specimen is completely removed and is received in the cavity 42 formed within the body of blade 24. During closure of the jaws, surface 30a of the block 30 rides on the surface epithelium of the biopsy specimen to prevent "tunneling" of the blade. Surface 30a thus serves as a guide surface which limits the depth of the bite taken by the blade.

In this manner, the specimen is initially undercut by the point 44 of the blade and is then sliced away from the cervix by the slicing action of the side portions 46 of the blade. No pinching or crushing action takes place. The only shearing that occurs takes place is when the side portions 46 of the blade move past the curved edges 48 (FIG. 1) which extend on opposite sides of the passage 22 of the receiver. When the jaws 20 and 26 are fully closed, the cutting edge of blade 24 is received in the passage 22, and the point 44 is located near the back of the passage, as shown in FIG. 2.

The teeth 28 remain embedded in the cervix as the jaws close and after closure they fall away. They serve to hold and stabilize the cervix during the biopsy bite in the area adjacent the biopsy specimen.

After the instrument has been used, the block 30 is slipped off of the upper jaw 26, and the block and used blade are disposed of in an appropriate manner. When the instrument is to be used again, another block is slipped onto the tongue 32 to provide a new clean sharp blade 24. The finger 36 serves as a stop which prevents block 30 from sliding upwardly off of tongue 32 as the jaws are closed during use of the instrument. The detent acts to maintain block 30 in the appropriate position on jaw 26. The dovetail joint provided by the tongue 32 and groove 34 permits the blades to be quickly and easily installed on and removed from the upper jaw 26. It should be pointed out that a T-shaped tongue and groove joint can be provided, as can other suitable connection for the block.

It is thus evident that the present invention provides an improved biopsy instrument which can be used to obtain good biopsy specimens that are not subjected to the pinching or crushing action that has been prevalent in the past. Due to the construction of the instrument and the manner in which it first undercuts the specimen and then slices it away from the cervix as the point 44 emerges, a full and undeformed layer of cervical epithelium is obtained for analysis, and the superficial surface epithelium is not scraped away or otherwise damaged.

From the foregoing, it will be seen that this invention is one well adapted to attain all the ends and objects hereinabove set forth together with other advantages which are obvious and which are inherent to the structure.

It will be understood that certain features and subcombinations are of utility and may be employed without reference to other features and subcombinations. This is contemplated by and is within the scope of the claims.

Since many possible embodiments may be made of the invention without departing from the scope thereof, it is to be understood that all matter herein set forth or shown in the accompanying drawing is to be interpreted as illustrative and not in a limiting sense.

Having thus described the invention, I claim:

1. An instrument for use in obtaining a cervical biopsy specimen, said instrument comprising:
    a pair of pincer arms each having a handle on one end and a jaw on the other end, said pincer arms being connected in a manner to effect closure of the jaws when the handles are moved together;
    gripping means on one jaw for gripping the cervix adjacent the biopsy specimen to hold and stabilize the cervix;
    a blade on the other jaw having the general shape of a U in section and presenting a sharp cutting edge on the leading edge thereof, said cutting edge having a sharp point located at the distal end of the cutting surface of said blade for undercutting the cervix and side portions on opposite sides of and trailing said point for slicing the cervix to remove the biopsy specimen during closure of said jaws, said blade presenting a cavity for receiving the biopsy specimen as same is cut from the cervix; and
    a recess in said one jaw located adjacent said gripping means and having a size and shape to receive said blade when said jaws are closed.

2. The invention of claim 1, wherein said gripping means includes a pair of teeth projecting from said one jaw for stabilizing the cervix when said one jaw is applied thereto.

3. The invention of claim 1, wherein said one jaw presents an edge portion adjacent said recess which cooperates with said blade to shear the biopsy specimen from the cervix as the blade enters said recess during closure of the jaws.

4. The invention of claim 1, wherein:
said blade has a hollow body which presents said cavity therein; and
said body terminates in a cutting edge which presents said point and side portions.

5. The invention of claim 1, including:
a block on which said blade is mounted; and
means for releasably attaching said block to said other jaw, whereby the blade can be removed following use and replaced with another blade.

6. The invention of claim 5, wherein said releasable attaching means includes:
a tongue on one of said block and other jaw; and
a groove on the other of said block and other jaw, said groove being adapted to closely receive said tongue to attach said block to said other jaw.

7. The invention of claim 6, including releasable detent means for holding said tongue in said groove.

8. The invention of claim 5, wherein said releasable attaching means includes:
a tongue projecting from said other jaw;
a groove in said block having a size and shape to closely receive said tongue therein to mount said block on said other jaw; and
stop means for preventing said tongue from passing completely through said groove in a direction toward said one jaw.

9. The invention of claim 8, including detent means for holding said tongue in said groove.

10. The invention of claim 8, wherein said stop means comprises a fixed stop member on said block located at the end of the groove nearer said one jaw to engage said tongue in a manner preventing the tongue from passing completely through the groove in a direction toward said one jaw.

11. The invention of claim 10, including releasable detent means for holding said tongue against said stop member.

12. A device for cutting a biopsy specimen from the cervix, said device comprising:
a pair of pincer arms each having a handle end and a jaw on the end opposite the handle end;
means for connecting said pincer arms in a manner to effect closing and opening of the jaws when the handle ends are moved toward and away from one another;
a pair of sharp teeth on one of said jaws for penetrating the cervix at spaced apart locations adjacent the biopsy specimen to hold and stabilize the cervix;
a blade on the other jaw having a curved cutting edge formed to present a sharp point located at the distal end thereof for undercutting the cervix and side portions on the opposite sides of said point for slicing the cervix to remove the biopsy specimen during closure of the jaws, said blade having a configuration to provide a cavity for receiving the biopsy specimen removed by said cutting edge; and
a recess in said one jaw adjacent said teeth for receiving the cutting edge of said blade when the jaws are closed, said recess presenting an edge which cooperates with said cutting edge to shear the biopsy specimen from the cervix as the cutting edge enters said recess during closure of the jaws, said point being located to enter said recess at a location between said teeth.

13. The invention of claim 12, including:
a block from which said blade projects; and
releasable means for attaching said block to said other jaw, thereby permitting the blade to be removed and replaced on said other jaw after use of the blade.

14. The invention of claim 13, including detent means for releasably holding said block on said other jaw.

15. The invention of claim 13, wherein said releasable means includes:
a tongue on said other jaw; and
a groove in said block having a size and shape to complement said tongue to permit the tongue to be received in the groove to hold said block on said other jaw.

16. The invention of claim 15, including stop means for preventing said tongue from passing completely through said groove in a direction toward said one jaw.

17. An instrument for use in obtaining a cervical biopsy specimen, said instrument comprising:
a first pincer arm having a handle on one end and a first jaw on the other end;
a second pincer arm having a handle on one end and a second jaw on the other end;
means for pivotally connecting said arms to close the first jaw on the second jaw along an arcuate path when the handles are moved together;
gripping means on said second jaw for application to the cervix to grip and stabilize same;
a cutting blade on said first jaw having a sharp cutting edge for slicing the biopsy specimen from the cervix;
a sharp point on said cutting edge located at the distal end of said blade to contact the cervix before the remainder of the cutting edge as said first jaw approaches said second jaw along said arcuate path, said point penetrating the cervix immediately upon contact therewith to undercut the cervix without applying pinching forces to the cervix as the first jaw closes;
side portions of said cutting edge on opposite sides of said point located to slice the cervix subsequent to undercutting thereof by said point, thereby severing the biopsy specimen from the cervix without deformation of the specimen; and
a cavity in said blade for receiving the biopsy specimen as same is severed from the cervix.

* * * * *